United States Patent [19]

Zähner et al.

[11] 4,406,905

[45] Sep. 27, 1983

[54] 2-PYRIDYL-2-THIAZOLINE-4-CARBOXYLIC ACID DERIVATIVES

[75] Inventors: Hans Zähner, Tübingen, Fed. Rep. of Germany; Hans-Ulrich Naegeli, Muttenz; Heinrich Peter, Binningen, both of Switzerland

[73] Assignee: Ciba-Geigy Corporation, Ardsley, N.Y.

[21] Appl. No.: 285,909

[22] Filed: Jul. 23, 1981

[30] Foreign Application Priority Data

Jul. 28, 1980 [CH] Switzerland .......................... 5755/80
Aug. 5, 1980 [CH] Switzerland .......................... 5925/80

[51] Int. Cl.³ ..................... A61K 31/44; C07D 409/04
[52] U.S. Cl. ..................... 424/263; 546/280; 435/120
[58] Field of Search ................ 546/280; 424/263

[56] References Cited

U.S. PATENT DOCUMENTS

| | | | |
|---|---|---|---|
| 3,592,905 | 7/1971 | Shen et al. | 424/270 |
| 3,842,172 | 10/1974 | Arlyan et al. | 424/263 |
| 3,852,293 | 12/1974 | Arlyan et al. | 424/263 |
| 4,260,765 | 4/1981 | Harrison et al. | 546/280 |

FOREIGN PATENT DOCUMENTS

| | | |
|---|---|---|
| 2053234 | 10/1970 | Fed. Rep. of Germany . |
| 2331246 | 1/1974 | Fed. Rep. of Germany . |
| 2729414 | 1/1978 | Fed. Rep. of Germany . |
| 1449669 | 9/1976 | United Kingdom . |

OTHER PUBLICATIONS

H. U. Naegeli and H. Zahner, Helv. Chim. Acta 63:6, 1400–1406.
I. Steffan and B. Prijs, Helv. Chim. Acta XLIV:V, 1429–1432.

*Primary Examiner*—Jane T. Fan
*Attorney, Agent, or Firm*—Irving N. Feit

[57] ABSTRACT

The invention relates especially to 2-(3'-hydroxypyrid-2'-yl)-2-thiazoline-4-carboxylic acid derivatives of the formula (I) and salts and also certain metal complexes of these compounds, processes for their manufacture, pharmaceutical agents containing such compounds and the use of these compounds.

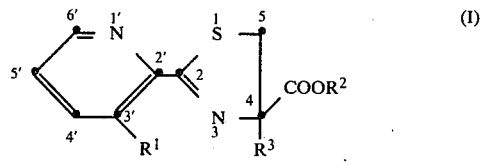

In the formula, $R^1$ represents free, etherified or esterified hydroxy, $R^2$ represents hydrogen or an aliphatic, carbocyclic or carbocyclic-aliphatic radical having 1–12 carbon atoms, and $R^3$ represents hydrogen or an unsubstituted aliphatic radical having 1–7 carbon atoms.

The compounds of the formula (I) can be used, for example, for the abstraction of heavy metals from the organism of warm-blooded animals and/or they have an antibiotic action.

22 Claims, No Drawings

2-PYRIDYL-2-THIAZOLINE-4-CARBOXYLIC ACID DERIVATIVES

The invention relates to novel derivatives of 2-pyrid-2'-yl)-2-thiazoline-4-carboxylic acid, processes for their manufacture, pharmaceutical preparations containing such compounds, and the use of these derivatives.

The invention relates especially to 2-(3'-hydroxypyrid-2'-yl)-2-thiazoline-4-carboxylic acid derivatives of the formula (I)

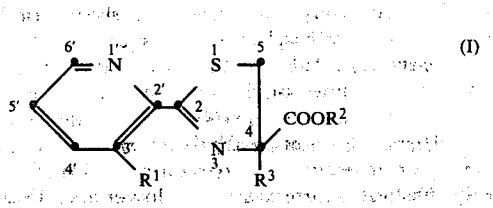

in a racemic or optically active form, in which
$R^1$ represents free, etherified or esterified hydroxy,
$R^2$ represents hydrogen or an aliphatic, carbocyclic or carbocyclic-aliphatic radical having 1–12 carbon atoms,
and
$R^3$ represents hydrogen or an unsubstituted aliphatic radical having 1–7 carbon atoms,
and salts of these compounds or metal ion complexes of such compounds in which the radical —$COOR^2$ represents a free carboxy group the acid proton of which has optionally been split off, processes for the manufacture of these compounds, pharmaceutical agents containing such compounds and the use of these compounds.

Etherified hydroxy $R^1$ represents especially hydroxy protected by etherification and/or denotes optionally substituted aliphatic, carbocyclic or carbocyclic-aliphatic hydrocarbyloxy or heterocyclyloxy having 1–12 carbon atoms. An aliphatic hydrocarbyloxy radical $R^1$ has especially 1–12, preferably 1–7 and more especially 1–4, carbon atoms and represents especially corresponding unsubstituted or substituted alkoxy, most especially unsubstituted alkoxy, for example methoxy.

The hydrocarbon moiety of a carbocyclic hydrocarbyloxy radical $R^1$ is especially a cycloaliphatic radical having 3–8, especially 5 or 6, ring members, more especially an unsubstituted or substituted cycloalkyl radical of that type, especially an unsubstituted cycloalkyl radical or a cycloalkyl radical substituted by lower alkyl, or is an aromatic mono- or bi-cyclic radical having 6 or 10 ring carbon atoms, respectively, for example a phenyl radical, most especially phenyl. Carbocyclic-aliphatic hydrocarbyloxy $R^1$ is especially aliphatic hydrocarbyloxy as defined above that is substituted by at least one carbocyclic radical of the type defined above.

Heterocyclyl in a heterocyclyloxy radical $R^1$ preferably represents unsubstituted or substituted, saturated or unsaturated, monocyclic five- or six-membered heterocyclyl having a nitrogen, oxygen or sulphur atom as ring member, especially saturated heterocyclyl, more especially saturated and unsubstituted heterocyclyl the free valency of which is adjacent to the hetero atom, for example 2-tetrahydropyranyl.

Esterified hydroxy $R^1$ can be derived from an organic or inorganic acid.

Of the inorganic acids there may be mentioned, for example, sulphuric and phosphoric acids.

Esterified hydroxy $R^1$ derived from an organic acid is especially acyloxy having 1–12 carbon atoms or sulphonyloxy. Acyloxy can represent formyloxy, but is preferably optionally substituted hydrocarbylcarbonyloxy or hydrocarbyloxycarbonyloxy. Therein, hydrocarbyl denotes an aliphatic radical having 1–11, especially 1–6, more especially 1–3, carbon atoms, a carbocyclic radical, i.e. a cycloaliphatic radical having 3–8, especially 5 or 6, ring members, or a mono- or bi-cyclic aromatic radical having 6 or 10 ring members, respectively, or a corresponding carbocyclic-aliphatic radical. The above-mentioned cycloaliphatic and aromatic radicals are preferably unsubstituted or substituted cycloalkyl radicals, especially unsubstituted cycloalkyl radicals or cycloalkyl radicals substituted by lower alkyl, and phenyl radicals, for example phenyl, respectively.

Sulphonyloxy is especially aromatic, more especially monocyclic aromatic, sulphonyloxy having 1–12 carbon atoms, for example toluenesulphonyloxy, or aliphatic sulphonyloxy having 1–12, especially 1–7, more especially 1–4, carbon atoms, especially unsubstituted or halogenated alkylsulphonyloxy.

Esterified hydroxy $R^1$ can especially represent hydroxy protected also by esterification.

An aliphatic, carbocyclic or carbocyclic-aliphatic radical $R_2$ represents preferably a carboxy-protecting group and/or has one of the following meanings.

An aliphatic radical $R^2$ has especially 1–12, preferably 1–7 and more especially 1–4, carbon atoms and represents especially corresponding unsubstituted or substituted alkyl, most especially unsubstituted alkyl, for example methyl.

A carbocyclic radical $R^2$ is especially a cycloaliphatic radical having 3–8, especially 5 or 6, ring members, more especially an unsubstituted or substituted cycloalkyl radical of that type, especially an unsubstituted cycloalkyl radical or a cycloalkyl radical substituted by lower alkyl, or is an aromatic mono- or bi-cyclic radical having 6 or 10 ring carbon atoms, respectively, for example a phenyl radical, such as, most especially, phenyl.

A carbocyclic-aliphatic radical $R^2$ is especially an aliphatic radical as defined above that is substituted by at least one carbocyclic radical of the type defined above, for example benzyl.

An unsubstituted aliphatic radical $R^3$ is especially lower alkyl, more especially methyl, and, in addition, lower alkenyl bonded by way of a saturated carbon atom.

The general definitions used hereinbefore and hereinafter preferably have the following meanings within the scope of the present description.

"Lower" signifies a radical having 1–7 carbon atoms. Lower alkyl is, for example, methyl, ethyl, n-propyl, isopropyl, n-butyl, isobutyl, sec.-butyl or tert.-butyl, also n-pentyl, neopentyl, n-hexyl or n-heptyl. Lower alkenyl is, for example, allyl or 2-butenyl. Cycloalkyl contains preferably 3–8, especially 5 or 6, ring members and is, for example, cyclopentyl or cyclohexyl. Phenyl-lower alkyl is, for example, benzyl, 1- or 2-phenylethyl or 3-phenylpropyl. Halogen is especially bromine but may also represent chlorine or iodine and also fluorine. Lower alkoxy is, for example, methoxy, also ethoxy, n-propoxy, isopropoxy, n-butoxy, isobutoxy or tert.-butoxy. Lower alkanoyloxy is, for example, acetoxy or propionyloxy. Lower alkoxycarbonyl is, for example, methoxycarbonyl or ethoxycarbonyl. Lower alkoxycarbonyloxy is, for example, methoxycarbonyloxy or ethoxycarbonyloxy. Five- or six-membered heterocyclyl having an oxygen, nitrogen or sulphur atom as ring member is, for example, tetrahydropyranyl, pyridyl, thienyl or furyl.

Substituents, for example of aromatic radicals, are optionally substituted lower alkyl, or phenyl optionally substituted, for example by lower alkyl, nitro, lower alkoxy and/or by halogen, or functional groups, for example basic groups, such as an optionally substituted amino group, or acid groups, such as optionally functionally modified, for example esterified, carboxy, for example carboxy or lower alkoxycarbonyl, or optionally etherified, esterified or protected hydroxy or oxo.

Monocyclic aromatic sulphonyloxy is, for example, p-toluenesulphonyloxy or benzenesulphonyloxy.

Lower aliphatic sulphonyloxy is, for example, methanesulphonyloxy.

Protecting groups, for example for the 3'-hydroxy group, and the methods by which they are introduced and split off are described, for example in "Protective Groups in Organic Chemistry", Plenum Press, London, New York 1973, and also in "Methoden der organischen Chemie", Houben-Weyl, 4th edition, vol. 15/1, Georg Thieme Verlag, Stuttgart 1974. It is characteristic of protecting groups that they can be split off readily, that is to say without undesired side reactions occurring, for example by solvolysis, reduction, photolysis or alternatively under physiological conditions.

Hydroxy-protecting groups are, for example, acyl radicals, such as lower alkanoyl optionally substituted, for example by halogen, such as 2,2-dichloroacetyl, or acyl radicals of carbonic acid semiesters, especially tert.-butoxycarbonyl, optionally substituted benzyloxycarbonyl, for example 4-nitrobenzyloxycarbonyl, or diphenylmethoxycarbonyl, or 2-halo-lower alkoxycarbonyl, such as 2,2,2-trichloroethoxycarbonyl, also trityl or formyl, or organic silyl or stannyl radicals, also etherifying groups that can readily be split off, such as tert.-lower alkyl, for example tert.-butyl, 2-oxa- or 2-thia-aliphatic or 2-oxa- or 2-thia-cycloaliphatic hydrocarbon radicals, especially 1-lower alkoxy-lower alkyl or 1-lower alkylthio-lower alkyl, for example methoxymethyl, 1-methoxyethyl, 1-ethoxyethyl, 1-methylthiomethyl, 1-methylthioethyl or 1-ethylthioethyl, or 2-oxa- or 2-thia-cycloalkyl having 5-7 ring atoms, for example tetrahydrofuryl or 2-tetrahydropyranyl or corresponding thia analogues, and also optionally substituted 1-phenyl-lower alkyl, such as optionally substituted benzyl or diphenylmethyl, there coming into consideration as substituents of the phenyl radicals, for example halogen, such as chlorine, lower alkoxy, such as methoxy, and/or nitro.

Carboxy groups are usually protected in esterified form, such ester groupings being split readily under mild conditions. Carboxy groups protected in this manner contain, as esterifying groups, such as the radical $R^2$, especially lower alkyl groups that are branched in the 1-position or suitably substituted in the 1- or 2-position. Preferred carboxy groups present in esterified form are, inter alia, tert.-lower alkoxycarbonyl, for example tert.-butoxycarbonyl; arylmethoxycarbonyl having one or two aryl radicals, the latter being phenyl radicals optionally mono- or poly-substituted, for example by lower alkyl, such as tert.-lower alkyl, for example tert.-butyl, lower alkoxy, such as methoxy, hydroxy, halogen, for example chlorine, and/or by nitro: such as benzyloxycarbonyl optionally substituted, for example as mentioned above, for example 4-nitrobenzyloxycarbonyl or 4-methoxybenzyloxycarbonyl, or diphenylmethoxycarbonyl optionally substituted, for example as mentioned above, for example diphenylmethoxycarbonyl or di-(4-methoxyphenyl)-methoxycarbonyl; or 1-lower alkoxy-lower alkoxycarbonyl, such as methoxymethoxycarbonyl, 1-methoxyethoxycarbonyl or 1-ethoxymethoxycarbonyl; or 1-lower alkylthio-lower alkoxycarbonyl, such as 1-methylthiomethoxycarbonyl or 1-ethylthioethoxycarbonyl; or aroylmethoxycarbonyl, in which the aroyl group represents benzoyl optionally substituted, for example by halogen, such as bromine: for example phenacyloxycarbonyl; or 2-halo-lower alkoxycarbonyl, for example 2,2,2-trichloroethoxycarbonyl, 2-bromoethoxycarbonyl or 2-iodoethoxycarbonyl; or 2-(tri-substituted silyl)-ethoxycarbonyl, in which each of the substituents, independently of the others, represents an aliphatic, araliphatic, cycloaliphatic or aromatic hydrocarbon radical that is optionally substituted, for example by lower alkyl, lower alkoxy, aryl, halogen and/or nitro, such as a corresponding, optionally substituted lower alkyl, phenyl-lower alkyl, cycloalkyl or phenyl: for example 2-tri-lower alkylsilylethoxycarbonyl, such as 2-trimethylsilylethoxycarbonyl or 2-(di-n-butyl-methyl-silyl)-ethoxycarbonyl, or 2-triarylsilylethoxycarbonyl, such as triphenylsilylethoxycarbonyl.

The above-mentioned organic silyl or stannyl radicals contain, as substituents of the silicon or tin atoms, preferably lower alkyl, especially methyl. Corresponding silyl or stannyl groups are especially tri-lower alkylsilyl, especially trimethylsilyl, also dimethyl-tert.-butyl-silyl, or correspondingly substituted stannyl, for example tri-n-butylstannyl.

Preferred protected carboxy groups are tert.-lower alkoxycarbonyl, such as tert.-butoxycarbonyl, and especially benzyloxycarbonyl optionally substituted, for example as mentioned above, such as 4-nitrobenzyloxycarbonyl, or diphenylmethoxycarbonyl, or more especially 2-(trimethylsilyl)-ethoxycarbonyl.

The salts of the compounds according to the invention are, especially, pharmaceutically acceptable, non-toxic salts, such as those of compounds of the formula (I) with acid groups, for example with a freecarboxy group. Such salts are especially internal salts, wherein a basic group, for example a basic nitrogen atom, present in the molecule, for example in the pyridine ring or in an optionally present free amino group, is protonated by a hydrogen ion originating from a molecule of the formula (I), and also metal salts and ammonium salts, such as alkali metal or alkaline earth metal salts, for example sodium, potassium, magnesium or calcium salts, and ammonium salts with ammonia or suitable organic amines, there coming into consideration for the salt formation especially aliphatic, cycloaliphatic, cycloaliphatic-aliphatic or araliphatic primary, secondary or tertiary mono-, di- or poly-amines, and also heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 4-aminobenzoic acid 2-diethylaminoethyl ester, lower alkyleneamines, for example 1-ethylpiperidine, cycloalkylamines, for example dicyclohexylamine, or benzylamines, for example N,N'-dibenzyl-ethylenediamine, also bases of the pyridine type, for example pyridine, collidine or quinoline. The compounds of the formula (I) can also form intermolecular (as opposed to intramolecular, i.e. zwitterionic)

acid addition salts, for example with inorganic acids, such as hydrochloric acid, sulphuric acid or phosphoric acid, or with suitable organic carboxylic or sulphonic acids, for example trifluoroacetic acid, or with amino acids, such as arginine and lysine. If several acid or basic groups are present, mono- or poly-salts can be formed. In the case of compounds of the formula (I) having an acid group, for example a free carboxy group, it is also possible for part of the molecule to be in the form of an internal salt and another part in the form of a normal salt.

For isolation and purification, pharmaceutically unacceptable salts also can be used. Only the pharmaceutically acceptable, non-toxic salts are used for therapeutic application and, for that reason, they are preferred.

The compounds of the formula I having a free carboxy group, wherein the proton of the carboxy group can have been split off, are capable of forming stable complexes with metal ions, such as heavy metal ions. Of the heavy metal ions, there may be mentioned especially those in the 3+ oxidation state, such as $Al^{3+}$ or $Cr^{3+}$, but, most especially, $Fe^{3+}$.

The addition of 2-(3'-hydroxy-pyrid-2'-yl)-4-methyl-2-thiazoline-4-carboxylic acid to an iron(III)-ethylenediaminetetraacetic acid disodium salt complex (log K=21.6) results in re-complexing, and, by following the course thereof polarographically, the decimal logarithm log K of the complex-forming constants K of 2-(3'-hydroxypyrid-2'-yl)-4-methyl-2-thiazoline-4-carboxylic acid-iron(III)-complex of 32.7 and its ligand number p of 3 can be obtained.

The substances of the formula (I) possess pharmacologically valuable properties. In particular, the compounds of the formula (I) are anti-bacterially active and can therefore be used in the form of pharmaceutical preparations, for example for the treatment of infections.

A 1% solution of 2-(3'-hydroxy-pyrid-2'-yl)-4-methyl-2-thiazoline-4-carboxylic acid in water was tested for antibiotic activity in an agar diffusion test against the following bacteria, the inhibition zones [mm] given in parentheses being observed: Sarcina lutea (13), Bac. subtilis (on synth. medium, 25), E. coli, supersensitive $EC_2$ (18), Proteus mirabilis (13), Proteus vulgaris (15) and Xanthomonas oryzae (22).

Owing to their ability to form stable complexes with heavy metal ions, especially with those in the 3+ oxidation state, such as $Al^{3+}$ or $Cr^{3+}$, but, most especially, with $Fe^{3+}$, the compounds of the formula (I) having a free 4-carboxy group, for example 2-(3'-hydroxy-pyrid-2'-yl)-4-methyl-2-thiazoline-4-carboxylic acid, prevent, for example, the deposition of iron-containing pigments in the tissues and, in cases where iron has been deposited in the organism, bring about elimination of the iron, for example, in haemochromatosis and haemosiderosis and also in cirrhosis of the liver. They can also be used for the elimination from the organism of other heavy metals, for example those mentioned above, or copper. For example, subcutaneous administration of 10 mg/kg of 2-(3'-hydroxy-pyrid-2'-yl)-4-methyl-2-thiazoline-4-carboxylic acid to rats brings about elimination of ferrithiocin detectable in the urine. The therapeutic daily dosage of the last-mentioned substance as an iron abstraction agent is, in the case of warm-blooded animals of approximately 70 kg body weight, for example in humans, 100–1000 mg, especially 300–700 mg, for example 500 mg. The dosage is preferably administered in several, for example three, individual doses, for example orally, or alternatively subcutaneously.

For the purpose of eliminating heavy metal ions, for example iron(III) ions, it is also possible to use compounds of the formula (I) having an esterified 4-carboxy group, the ester grouping of which is readily saponified under physiological conditions (prodrug forms).

On the other hand, the iron-containing complexes may, in certain cases, be used as iron donors, for example in commercially useful animals.

For example, the iron complex of 2-(3'-hydroxy-pyrid-2'-yl)-4-methyl-2-thiazoline-4-carboxylic acid can be used for the prophylaxis and therapy of iron deficiency anaemia in suckling pigs. For this purpose, two doses, which correspond to a combined iron content of 100 mg per piglet, are administered, after 11 and 16 days of life, directly to the stomach by means of a rubber probe, in the form of a finely divided suspension in 40 ml of 0.6 M phosphate buffer of pH 7.4. The weight of the piglets at birth is, on average, 1.7 kg, after 11 days of life 3–4 kg, after 16 days of life 3.7–5.1 kg and after 22 days of life 4.5 to 6.5 kg. Measurement of the haemoglobin concentration after 11 test days (22 days of life) shows significantly increased values in comparison with a negative control (corresponding buffer solution without active substance).

In testing for acute toxicity in mice (5 animals of 20–25 g), 2-(3'-hydroxy-pyrid-2'-yl)-4-methyl-2-thiazoline-4-carboxylic acid was found to be completely tolerable at a dosage of 100 mg/kg both when administered perorally and when administered subcutaneously.

Compounds of the formula (I) in which the functional groups are protected are used especially as intermediates for the manufacture of those compounds of the formula (I) in which the functional groups are present in free form.

The invention relates especially to compounds of the formula (I) in which $R^1$ represents free hydroxy, hydrocarbyloxy, hydrocarbylcarbonyloxy or hydrocarbyloxycarbonyloxy, hydrocarbyl denoting an aliphatic radical having 1–7 carbon atoms, a cycloaliphatic radical having 5 or 6 ring members, a phenyl radical, or an aliphatic radical having 1–7 carbon atoms that is substituted by at least one cycloaliphatic radical of that type or by at least one phenyl radical, or in which $R^1$ represents monocyclic five- or six-membered heterocyclyloxy having a nitrogen, oxygen or sulphur atom as ring member, or monocyclic aromatic or lower aliphatic sulphonyloxy, in which $R^2$ represents hydrogen, an aliphatic radical having 1–7 carbon atoms, a cycloaliphatic radical having 5 or 6 ring members, a phenyl radical, or an aliphatic radical having 1–7 carbon atoms that is substituted by at least one cycloaliphatic radical of that type or by at least one phenyl radical, and in which $R^3$ represents hydrogen or lower alkyl.

The invention relates more especially to compounds of the formula (I) in which $R^1$ represents free hydroxy, alkoxy having 1–12 carbon atoms, monocyclic aromatic sulphonyloxy, lower alkylsulphonyloxy, hydrocarbylcarbonyloxy or hydrocarbyloxycarbonyloxy, hydrocarbyl representing lower alkyl, cycloalkyl having 3–8 carbon atoms, a monocyclic aromatic hydrocarbon radical or phenyl-lower alkyl, and in which $R^2$ represents a hydrocarbyl radical of that kind or hydrogen and $R^3$ represents hydrogen or lower alkyl.

The invention relates preferably to compounds of the formula (I) in which $R^1$ represents free hydroxy, lower alkoxy or lower alkanoyloxy, or phenyloxy or benzyloxy each of which is unsubstituted or substituted by halogen, lower alkyl or lower alkoxy, and in which $R^2$ represents hydrogen, lower alkyl, or a phenyl or phenyl-lower alkyl radical, and $R^3$ represents hydrogen or lower alkyl.

Especially preferred are compounds of the formula (I) in which $R^1$ represents free hydroxy or lower alkoxy, $R^2$ represents hydrogen or lower alkyl and $R^3$ represents methyl, and salts of these compounds and iron ion complexes of such compounds having a free 4-carboxy group.

Emphasis should be given to compounds of the formula (I) in which $R^1$ represents hydroxy or methoxy, $R^2$ represents hydrogen or methyl and $R^3$ represents hydrogen or methyl, and the salts thereof.

Special emphasis should be given to the above-mentioned compounds of the formula (I) in which $R^2$ represents hydrogen or a physiologically tolerable radical that can be split off readily under physiological conditions, and the salts thereof, especially pharmaceutially acceptable salts and iron complexes, especially iron(III) complexes.

Most especially preferred are compounds of the formula (I) in which $R^3$ represents methyl, and the salts thereof.

The invention relates especially to the compounds of the formula (I) mentioned in the Examples, and to salts, especially pharmaceutically acceptable salts, most especially to 2-(3'-hydroxy-pyrid-2'-yl)-4-methyl-2-thiazoline-4-carboxylic acid, especially in the optically active form obtainable according to Example 2.

The compounds of the formula (I) according to the invention and salts of those compounds and metal complexes of such compounds, in which the radical $COOR^2$ represents a free carboxy group the acid proton of which has optionally been split off, can be manufactured by chemical synthesis according to processes known per se. They are manufactured, for example, by reacting a picolinic acid derivative of the formula (II)

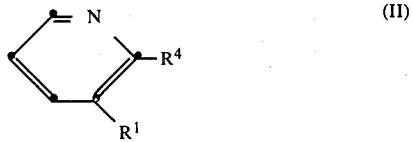

(II)

in which $R^1$ represents free, etherified or esterified hydroxy, with the proviso that hydroxy or other functional groups are optionally in protected form, and $R^4$ represents a cyano or carboxy group, or a reactive functional derivative of the same, with a 2-amino-3-mercapto-2-$R^3$-propionic acid derivative of the formula (III)

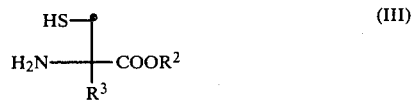

(III)

in which the substituents are as defined above, with the proviso that one or more functional groups present in the compound are optionally in protected form, or with a reactive functional derivative thereof and, if desired, splitting off optionally present protecting groups and/or, in a resulting compound of the formula (I), esterifying or etherifying a 3'-hydroxy group or converting an esterified or etherified hydroxy group into a free hydroxy group and/or esterifying a carboxy group with an esterifying agent that contains the radical $R^2$ or saponifying an esterified carboxy group, and/or converting the compounds of the formula (I) into their acid addition salts or converting the compounds of the formula (I) having a free carboxy group into their metal salts or into heavy metal complexes and, if desired, separating racemates into the optically active forms.

A reactive functional derivative of a carboxy group $R^4$ is, for example, an acid anhydride, an activated ester or an activated amide.

Of the anhydrides, the mixed anhydrides are especially suitable. Mixed anhydrides are, for example, those with inorganic acids, such as hydrohalic acids, i.e. the corresponding acid halides, for example chlorides or bromides, also with hydrazoic acid, i.e. the corresponding acid azides, with a phosphorus-containing acid, for example phosphoric acid, diethylphosphoric acid or phosphorous acid, or with a sulphur-containing acid, for example sulphuric acid, or with hydrocyanic acid. Further mixed anhydrides are, for example, those with organic carboxylic acids, such as with lower alkanecarboxylic acids optionally substituted, for example by halogen, such as fluorine or chlorine, for example pivalic acid or trichloroacetic acid, or with semiesters, especially lower alkyl semiesters of carbonic acid, such as the ethyl or isobutyl semiester of carbonic acid, or with organic, especially aliphatic or aromatic, sulphonic acids, for example p-toluenesulphonic acid.

Of the activated esters, there may be mentioned, for example: esters with vinylogous alcohols, (i.e. enols, such as vinylogous lower alkenols), or iminomethyl ester halides, such as dimethyliminomethyl ester chloride (prepared from the carboxylic acid and, for example, dimethyl-(1-chloroethylidene)-iminium chloride of the formula $(CH_3)_2N^{\oplus}=C(Cl)CH_3$ $Cl^{\ominus}$, which can be obtained, for example, from N,N-dimethylacetamide and phosgene), or aryl esters, such as preferably suitable substituted phenyl esters, for example phenyl esters substituted by halogen, such as chlorine, and/or by nitro, for example 4-nitrophenyl ester, 2,3-dinitrophenyl ester or 2,3,4,5,6-pentachlorophenyl ester, N-heteroaromatic esters, such as N-benztriazole esters, for example 1-benztriazole ester, or N-diacylimino esters, such as N-succinylimino or N-phthalylimino ester.

Suitable activated amides are, for example, especially imidazolides, also 1,2,4-triazolides, tetrazolides or 1,2,4-oxadiazolinonides.

The activation of a carboxy group $R^4$ in the picolinic acid derivative can also be effected in situ.

A reactive functional derivative of a 2-amino-3-mercapto-2-$R^3$-propionic acid derivative of the formula (III) is a compound in which the amino and/or mercapto group is activated for the reaction with the carboxy group of a compound of the formula (II), that is to say is present in nucleophilic form. The amino group is activated, for example, by reaction with a phosphite.

A preferred form of the reaction according to the invention is the reaction of a compound of the formula (II) in which $R^4$ represents cyano with a cysteine derivative of the formula (III), which is carried out, for example, as described in the Examples.

The reaction of free carboxy $R^4$ with the desired cysteine derivative is preferably carried out in the presence of a suitable condensation agent or under dehydrating conditions, for example while removing the water of reaction by azeotropic distillation. Customary condensation agents are, for example carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulphonate or 2-tert.-butyl-5-methyl-isoxazolium perchlorate, or a suitable acylamino compound, for example 2-ethoxy-1-ethoxycarbonyl-1,2-dihydroquinoline. The condensation reaction is carried out preferably in an anhydrous reaction medium, preferably in the presence of a solvent or diluent, for example methylene chloride, benzene or tetrahydrofuran and, if necessary, while cooling or heating and/or in an inert gas atmosphere.

Compounds of the formula (I) in which $R^3$ represents lower alkyl are manufactured in a manner known per se by removing a proton in the 4-position, by means of a base, from a compound of the formula (I) in which $R^3$ represents hydrogen and in which $R^1$ and $R^2$ are as defined for formula (I), with the proviso that functional groups present therein are, if desired, in protected form, and reacting the resulting intermediate with an alkylating agent that transfers the radical $R^3$ and in which the alkyl carbon atom that enters into the new bond carries a positive partial charge and, if desired, splitting off optionally present protecting groups and/or, in a resulting compound of the formula (I), esterifying or etherifying a 3'-hydroxy group or converting an esterified or etherified hydroxy group into a free hydroxy group and/or esterifying a carboxy group with an esterifying agent that contains the radical $R^2$ or saponifying an esterified carboxy group, and/or converting the compounds of the formula (I) into their acid addition salts or converting the compounds of the formula (I) having a free carboxy group into their metal salts or into heavy metal complexes and, if desired, separating racemates into the optically active forms.

Suitable bases are, for example, metallating reagents, such as unsubstituted or substituted alkali metal amides, for example sodium amide, lithium amide or preferably sterically hindered lithium amides, for example lithium trimethylsilylamide, lithium isopropyl-cyclohexylamide or lithium dialkylamides, such as lithium diisopropylamide, or alkali metal lower alkyl compounds, such as methyllithium or n- or tert.-butyllithium, and also alkali metal hydrides, such as sodium hydride.

If the reaction is carried out under phase transfer conditions or in the presence of suitable complex formers for the base cation, such as Crown ethers, for example 18-Crown-6, weaker bases, such as alkali metal hydroxides, for example potassium hydroxide, are also suitable.

Suitable alkylating agents that transfer the radical $R^3$ are, for example, lower alkyl or lower alkenyl compounds having a nucleophilic leaving group, for example halides, such as chlorides, bromides or, especially, iodides, for example methyl iodide or allyl bromide, or sulphonic acid esters or sulphuric acid esters of unsubstituted aliphatic alcohols having 1–7 carbon atoms, for example toluenesulphonic acid isopropyl ester, methylsulphonic acid butyl ester or diethyl sulphate.

The metallation carried out with the above-mentioned alkali metal amides, alkali metal hydrides or alkali metal lower alkyl compounds is carried out in an inert, aprotic solvent and under protective gas, for example in a hydrocarbon, for example hexane, benzene, toluene or xylene, a weakly polar ether, for example diethyl ether, tetrahydrofuran or dioxan, or an acid amide, for example hexamethylphosphoric acid triamide, or mixtures thereof. The reaction temperature lies between approximately $-80°$ and approximately room temperature, depending mainly on the melting point of the solvent or solvent mixture and on the reactivity of the particular metallating reagent in the chosen solvent, but also on the solubility and the reactivity of the substrate.

Alkylation takes place at a far higher temperature than the metallation and is generally effected by introducing the alkylating agent into the reaction vessel after metallation is complete and allowing the reaction vessel to warm up.

Further details for carrying out the metallation and alkylation reactions, which are analogous to those described above, are described, for example, in Houben-Weyl, Methoden der Organischen Chemie, vol. XIII/1, Thieme Verlag, Stuttgart 1970.

A further process for the manufacture of compounds of the formula (I) in which $R^1$ represents a free hydroxy group and/or $R^2$ represents hydrogen is characterised in that at least one protecting group in a compound of the formula (I) in which $R^1$ represents a protected hydroxy group and/or $COOR^2$ represents a protected carboxy group, is split off.

Compounds of the formula (I) in which $R^3$ represents a methyl group and the other substituents have the meanings indicated for formula (I), and the above-mentioned salts and metal complexes of these compounds can be manufactured, apart from by the analogous processes described hereinbefore, also by a novel inventive process which is characterised in that the strain *Streptomyces antibioticus* Waksman et Henrici Tu 1998 (DSM 1865) or a mutant of this strain that forms 2-(3'-hydroxy-pyrid-2'-yl)-4-methyl-2-thiazoline-4-carboxylic acid is cultured aerobically in an aqueous nutrient solution containing a carbon and nitrogen source and inorganic salts, and the 2-(3'-hydroxy-pyrid-2'-yl)-4-methyl-2-thiazoline-4-carboxylic acid or a stable heavy metal complex of that acid is isolated from the nutrient solution and, if desired, the 2-(3'-hydroxy-pyrid-2'-yl)-4-methyl-2-thiazoline-4-carboxylic acid or a salt of the same is liberated from the heavy metal complex and, if desired, a 3'-hydroxy group is esterified or etherified or an esterified or etherified hydroxy group is converted into a free hydroxy group and/or a carboxy group is esterified with an esterification agent that contains the radical $R^2$ or an esterified carboxy group is saponified, and/or the compounds of the formula (I) are converted into their acid addition salts or the compounds of the formula (I) having a free carboxy group are converted into their metal salts or into heavy metal complexes.

It is possible that also compounds of the formula I in which $R^3$ has the meanings given above can be manufactured by the microbiological method mentioned by adding cysteine or corresponding cysteine derivatives to the nutrient solution.

The strain *Streptomyces antibioticus* Tu 1998 was deposited under the designation DSM 1865 at the Deutsche Sammlung von Mikroorganismen (German Collection of Microorganisms), Griesebachstrasse 8, D-3400 Gottingen on 16th June, 1980.

The strain is characterised by the following features:

Its spores are ellipsoid, $0.6-1.4\mu \times 0.5-1.2\mu$ in size, and have a smooth to slightly nodular (possibly as a consequence of the preparation) surface. The aerial mycelium is initially greyish white and, with increasing maturity, becomes grey to ash grey.

The spore chains are monopodially branched and only slightly undulated. On peptone-containing culture media, especially on "peptone-iron-agar", the strain forms a dark melanine-like pigment. The substrate mycelium is dark to brownish red. As a result of the rubromycins which are formed at the same time on some culture media, the substrate appears to be discoloured wine-red to brownish red.

The mutants forming the antibiotic can be obtained, for example, under the action of ultra-violet rays or X-rays or of chemical mutagens, for example N-methyl-N'-nitro-N-nitroso-guanidine.

As carbon source, there may be mentioned, for example: assimilible carbohydrates, for example glucose, saccharose, lactose, mannitol, starch, glycerin. As nitrogen-containing nutrient substances there may be mentioned: amino acids, peptides and proteins and their degradation products, such as peptone and tryptone, also meat extracts, water-soluble parts of cereal grains, such as maize and wheat, of distillation residues from alcohol manufacture, of yeast, beans, especially soya plants, of seeds, for example of cotton plants etc., or alternatively ammonium salts and nitrates. Other inorganic salts that may be present in the nutrient solution are, for example, chlorides, carbonates, sulphates or phosphates of alkali metals or alkaline earth metals, of magnesium, iron, zinc and manganese.

Culturing is carried out aerobically, that is, for example, in a still surface culture or, preferably, submers while shaking or stirring with air or oxygen in a shaking flask or in known fermenters. A suitable temperature is one between 18° and 40° C., preferably approximately 27° C. The nutrient solution exhibits a substantial antibiotic action generally after 3 to 7 days. Culturing is preferably carried out in several stages, i.e. one or several pre-cultures are first prepared in a liquid nutrient medium and are then transferred by inoculation to the actual production medium, for example in a ratio of 1:20.

Preferably, the pre-culture is cultured on the same nutrient solution and is left to grow for approximately 48 hours. The producer strain secretes the 2-(3'-hydroxy-pyrid-2'-yl)-4-methyl-2-thiazoline-4-carboxylic acid (iron-free) into the culture solution.

In the fermentation according to the invention, apart from 2-(3'-hydroxy-pyrid-2'-yl)-4-methyl-2-thiazoline-4-carboxylic acid, other products also are produced among which it has been possible to identify β- and γ-rubromycins which were originally described as metabolites of *Streptomyces collinus* Lindenbein [H. Brockmann and K. H. Renneberg, Naturwiss. 40, 59–60 (1953); H. Brockmann, W. Lenk, G. Schwanthe and A. Zeeck, Tetrahedron Letters 1966, 3525; H. Brockmann and A. Zeeck, Chem. Ber. 103, 1709–1726 (1970)].

Isolation of 2-(3'-hydroxy-pyrid-2'-yl)-4-methyl-2-thiazoline-4-carboxylic acid can be carried out according to methods known per se having regard to the chemical, physical and biological properties of the antibiotic. Preferably, there is added to the cultures, at a pH near the neutral point, for example at pH 7.5, a heavy metal salt that forms stable isolatable complexes with the antibiotic, for example iron(III) chloride hexahydrate or other iron(III) salts, in an amount sufficient for complexing the antibiotic.

Upon the addition of iron(III) salts, a characteristically coloured iron complex ("ferrithiocin") is formed which, at neutral pH and when saturated with sodium chloride, can be extracted with ethyl acetate. Extraction can also be carried out successfully with methylene chloride/isopropanol 85:15 at pH 8.5 according to the Extrelut ® process [J. Breiter, Kontakte Merck, 3, 9–14 (1977)], the iron ions from the packing of the extraction column being sufficient for complex formation. The extracts are purified by extraction of the lipophilic constituents with methylene chloride from water and chromatography over Sephadex LH-20. The iron complex ferrithiocin so obtained can be crystallised from methanol/acetonitrile/toluene without further purification.

In the mild oxidation of this iron complex with potassium permanganate in aqueous sodium hydroxide solution, an oxidation product having a molecular ion peak m/z=192 is produced. By high-resolution mass spectrometry it is assigned the molecular formula $C_9H_8N_2OS$. In the $^1H$-NMR spectrum of the oxidation product, an olefinic singlet appears at 6.94 ppm instead of the AB system of the original methylene group. At the same time, the singlet of the tertiary methyl group is shifted to a deeper field at 2.48 ppm.

On the basis of these data, the oxidation product is 3-hydroxy-2-(4'-methyl-thiazol-2'-yl)-pyridine of the formula

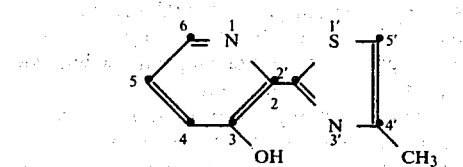

Treatment of the iron complex ferrithiocin with $OH^\ominus$ ions in sufficient concentration, preferably in the form of an alkali metal hydroxide, for example with 1 N NaOH, removal of ferric hydroxide by filtration and acidification to pH 3 yields 2-(3'-hydroxy-pyrid-2'-yl)-4-methyl-2-thiazoline-4-carboxylic acid in the form of sulphur-yellow felt-like needles. The mass spectrum shows a molecular ion peak with m/z 238, to which, by high resolution, the molecular formula $C_{10}H_{10}N_2O_3S$ is assigned. Microanalysis matches best a compound having a molecule of water which, however, upon drying at high temperature, is lost again. In the IR absorption spectrum, the broad absorption band between 3600 and 2200 cm$^{-1}$ and also a carbonyl band at 1695 cm$^{-1}$ point to the presence of a carboxy group. In the $^{13}C$-NMR spectrum, the signal at 180 ppm is assigned to the carboxy carbon atom. The third oxygen atom is assigned to a phenolic OH group bonded by a hydrogen bridge. In the IR spectrum the associated band is found at 3550 cm$^{-1}$ and in the $^1H$-NMR spectrum of the corresponding 4-carboxylic acid methyl ester and of the above-mentioned oxidation product 3-hydroxy-2-(4'-methyl-thiazol-2'-yl)-pyridine a singlet is found at 12 ppm that can be exchanged for $D_2O$. A methyl group bonded in the tertiary position gives in the $^1H$-NMR spectrum a singlet at 1.61 ppm and a methylene group an AB system at 3.30 and 3.75 ppm with J=12 Hz. In the $^{13}C$-NMR spectrum, the corresponding signals are found as a quartet at 25.5 ppm and as a triplet at 40.7 ppm. The three hydrogen atoms still remaining according to the complete formula are bonded to an aromatic ring (signals at 7.45 ppm, 2H, and 8.18 ppm, 1H, in the $^1H$-NMR; doublets at 126.0, 128.1 and 141.1 ppm in the $^{13}C$-NMR spectrum).

Acid hydrolysis provides information on the nature and the substitution pattern of the aromatic ring of the iron-free compound obtained by treatment of the ferrithiocin with sodium hydroxide solution. After treatment with 6 N HCl at 90° for 1 hour, an aromatic carboxylic acid ($C_6H_5NO_3$, $M^+$ 139) is isolated by means of preparative thin-layer chromatography, from which, by esterification with diazomethane, a compound is obtained which is identified as 3-hydroxy-picolinic acid methyl ester. The structure is derived from the mass spectrum: $M^+=253$, m/z 223 ($M^+$—$CH_2=O$, MacLafferty transposition), 221 ($M^+$—$CH_3OH$), 95 ($M^+$—$CH_2=CO$) etc. and from the $^1$NMR and IR spectra which agree with the spectra of an authentic sample of this compound.

A further component of the acid hydrolysis, which can be coloured on thin-layer (TLC)-plates with nitroprussidesodium [see G Tonnies and J. J. Kolb, Anal. Chemistry 23, 823 (1951)], can be isolated by means of chromatography over CM Sephadex C-25 in pyridine-/acetate buffer of pH 5.

This compound is found to be stable only at low temperatures (−20° C.) and under nitrogen. A more stable derivative, which according to TLC and $^1$NMR spectroscopy is not entirely uniform, of the formula

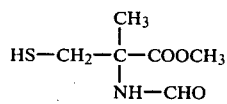

is obtained by treatment of the crude product with diazomethane in absolute dimethylformamide with the addition of $BF_3$-ether complex and subsequent purification on preparative TLC plates. In the $^1$H-NMR spectrum, a methyl ester signal is found at 3.78 ppm and, at 1.67 ppm, the singlet of a tertiary methyl group. At 1.35 ppm a double doublet appears corresponding to 1 H with a coupling constant J of 8 and 10 Hz which disappears upon the addition of $D_2O$. This signal is assigned to a primary SH group. The coupling partner, a vicinal $CH_2$ group, is indicated by 2 double doublets at 2.96 ppm with J of 10 and 14 Hz and also at 3.55 with J of 8 and 14 Hz. This signal group is reduced to 2 doublets with J of 14 Hz upon the addition of $D_2O$. An N-formyl group is recognised on account of a doublet with J of 2 Hz at 8.17 ppm and also on account of the broad signal of an amide proton at 6.6 ppm. Obviously, the formyl group has been transferred from the solvent DMF to the nitrogen of the degradation product under the chosen reaction conditions. By means of these signals the above structure (N-formyl-2-methylcysteinemethyl ester) is derived for this degradation product. Although the mass spectrum shows no molecular peak ($C_6H_{11}NO_3S$, m.w. 177), the observed fragments are well matched to the structure: m/z 132 ($M^+$—$NH=CH$-$OH$ MacLafferty transposition, 100% Int.), 118 ($M^+$—$COOCH_3$), 100 ($M^+$—$NH=CH$-$OH$ and $CH_3OH$). This degradation result indicates a thiazoline derivative.

Compounds of the formula (I) in which the 4-carboxy group has been esterified (see below) or removed, for example by mild oxidation with potassium permanganate, may well exhibit a colour reaction with $FeCl_3$ solution but no longer form any complexes that can be isolated. This indicates that the free 4-carboxy group is essential for complex formation.

The compounds of the formula (I) obtainable according to the invention can be converted in a manner known per se into other compounds of the formula (I).

In the compounds of the formula (I) in which $R^1$ represents a free hydroxyl group, the latter can be etherified or esterified according to methods known per se. A free 4-carboxy group can be esterified.

Suitable agents for etherifying the 3'-OH group and for esterifying the carboxy group are, for example, corresponding diazo compounds, such as optionally substituted diazo-lower alkanes, for example diazomethane, diazoethane, diazo-n-butane or diphenyldiazomethane. These reagents are employed in the presence of a suitable inert solvent, such as an aliphatic, cycloaliphatic or aromatic hydrocarbon, such as hexane, cyclohexane, benzene or toluene, a halogenated aliphatic hydrocarbon, for example methylene chloride, or an ether, such as a di-lower alkyl ether, for example diethyl ether, or a cyclic ether, for example tetrahydrofuran or dioxan, or a solvent mixture, and, depending on the diazo reagent, while cooling, at room temperature or while heating slightly, and, if necessary, in a closed vessel and/or under an inert gas atmosphere, for example a nitrogen atmosphere.

If, for example, 2-(3'-hydroxy-pyrid-2'-yl)-4-methyl-2-thiazoline-4-carboxylic acid is treated at 0° with diazomethane, the 4-carboxylic acid methyl ester is obtained which, in the IR spectrum ($CHCl_3$), shows at 1735 cm$^{-1}$ the band of an aliphatic ester and, in the $^1$H-NMR spectrum, an additional singlet corresponding to 3 H at 3.77 ppm. If the same reaction is carried out exhaustively at room temperature, the phenolic 3'-hydroxy group also is methylated, which is apparent from the disappearance of the signal at 12 ppm and the appearance of a singlet at 3.88 ppm in the $^1$H-NMR.

Further suitable agents for etherifying the 3'-OH group and for esterifying the carboxy group are esters of corresponding alcohols, especially those with strong inorganic or organic acids, such as mineral acids, for example hydrohalic acids, such as hydrochloric acid, hydrobromic acid or hydriodic acid, also sulphuric acid, or halosulphuric acid, for example fluorosulphuric acid, or strong organic sulphonic acids, such as lower alkanesulphonic acids optionally substituted, for example by halogen, such as fluorine, or aromatic sulphonic acids, such as, for example, benzenesulphonic acids optionally substituted by lower alkyl, such as methyl, by halogen, such as bromine, and/or by nitro, for example methanesulphonic acid, trifluoromethanesulphonic acid or p-toluenesulphonic acid. Such esters are, inter alia, lower alkyl halides, di-lower alkyl sulphates, such as dimethyl sulphate, also fluorosulphonic acid esters, such as fluorosulphonic acid lower alkyl esters, for example fluorosulphonic acid methyl ester, or optionally halogen-substituted methanesulphonic acid lower alkyl esters, for example trifluoromethanesulphonic acid methyl ester. They are usually used in the presence of an inert solvent, such as an optionally halogenated, such as chlorinated, aliphatic, cycloaliphatic or aromatic hydrocarbon, for example methylene chloride, an ether, such as dioxan or tetrahydrofuran, or a mixture. At the same time, suitable condensation agents are preferably used, such as alkali metal carbonates or bicarbonates, for example sodium or potassium carbonate or bicarbonate (usually together with a sulphate), or organic bases, such as usually sterically hindered tri-lower alkylamines, for example N,N-diisopropyl-N-ethylamine (preferably together with halosulphonic acid lower alkyl esters or optionally halogen-substituted methanesulphonic acid lower alkyl esters), the operation being carried out while cooling, at room temperature or while heating, for example at temperatures of from approximately −20° C. to approximately 50° C. and, if necessary, in a closed vessel and/or in an inert gas atmosphere, for example a nitrogen atmosphere.

By phase-transfer catalysis [see Dehmlow, Angewandte Chemie, vol. 5, page 187 (1974)] the above-described etherification reaction can be considerably accelerated. As phase-transfer catalysts, there may be used quaternary phosphonium salts and especially quaternary ammonium salts, such as optionally substituted tetraalkylammonium halides, for example tetrabutylammonium chloride, bromide or iodide, or alternatively benzyltriethylammonium chloride, in catalytic or up to equimolar amounts. As the organic phase there can be used any one of the solvents that is not miscible with water, for example one of the optionally halogenated, such as chlorinated, lower aliphatic, cycloaliphatic or aromatic hydrocarbons, such as tri- or tetra-chloroethylene, tetrachloroethane, carbon tetrachloride, chlorobenzene, toluene or xylene. In the case of compounds that are sensitive to bases, the alkali metal carbonates or bicarbonates, for example potassium or sodium carbonate or bicarbonate, alkali metal phosphates, for example potassium phosphate, and alkali metal hydroxides, for example sodium hydroxide, which are suitable as condensation agents can be added to the reaction mixture titrimetrically, for example by means of an automatic titrating apparatus so that, during etherification, the pH remains between approximately 7 and approximately 8.5.

Further agents for etherifying the 3'-OH group or for esterifying the 4-carboxy group are corresponding trisubstituted oxonium salts (so-called Meerwein salts), or disubstituted carbenium or halonium salts, in which the substituents are the etherifying radicals, for example tri-lower alkyloxonium salts, and also di-lower alkoxycarbenium or di-lower alkylhalonium salts, especially the corresponding salts with complex, fluorine-containing acids, such as the corresponding tetrafluoroborates, hexafluorophosphates, hexafluoroantimonates, or hexachloroantimonates. Such reagents are, for example, trimethyloxonium or triethyloxonium hexafluoroantimonate, hexachloroantimonate, hexafluorophosphate or tetrafluoroborate, dimethoxycarbenium hexafluorophosphate or dimethylbromonium hexafluoroantimonate. These etherifying agents are used preferably in an inert solvent, such as an ether or a halogenated hydrocarbon, for example diethyl ether, tetrahydrofuran or methylene chloride, or in a mixture thereof, if necessary in the presence of a base, such as an organic base, for example a preferably sterically hindered tri-lower alkylamine, for example N,N-diisopropyl-N-ethylamine, and while cooling, at room temperature or while heating slightly, for example at from approximately −20° C. to approximately 50° C., if necessary in a closed vessel and/or in an inert gas atmosphere, for example a nitrogen atmosphere.

Further etherifying agents are, finally, corresponding 1-substituted 3-aryltriazene compounds, in which the substituent represents the etherifying radical and aryl preferably represents optionally substituted phenyl, for example lower alkylphenyl, such as 4-methylphenyl. Such triazene compounds are 3-aryl-1-lower alkyltriazenes, for example 3-(4-methylphenyl)-1-methyltriazene, 3-(4-methylphenyl)-1-ethyltriazene or 3-(4-methylphenyl)-1-isopropyltriazene. These reagents are usually used in the presence of inert solvents, such as optionally halogenated hydrocarbons or ethers, for example benzene, or solvent mixtures, and while cooling, at room temperature and, preferably, at elevated temperature, for example at from approximately 20° C. to approximately 100° C., if necessary in a closed vessel and/or in an inert gas atmosphere, for example a nitrogen atmosphere.

The conversion of free carboxy in a compound of the formula (I) into esterified carboxy can also be carried out, for example, by reacting a compound of the formula (I) in which other, optionally present functional groups are optionally in protected form, or a reactive functional carboxy derivative, including a salt thereof, with a corresponding alcohol or a reactive functional derivative thereof.

The esterification of free carboxy with the desired alcohol is carried out in the presence of a suitable condensation agent. Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium 3'-sulphonate and 2-tert.-butyl-5-methyl-isoxazolium perchlorate, or a suitable acylamino compound, for example 2-ethoxy-1-ethoxycarbonyl-1,2-dihydroquinoline. The condensation reaction is carried out preferably in an anhydrous reaction medium, preferably in the presence of a solvent or diluent, for example methylene chloride, dimethylformamide, acetonitrile or tetrahydrofuran and, if necessary, while cooling or heating and/or in an inert gas atmosphere.

Suitable reactive functional derivatives of the carboxy compounds of the formula (I) that are to be esterified are, for example, anhydrides, especially mixed anhydrides, and activated esters.

Mixed anhydrides are, for example, those with inorganic acids, such as hydrohalic acids, i.e. the corresponding acid halides, for example chlorides or bromides, also hydrazoic acids, that is to say the corresponding acid azides, and phosphorus-containing acids, for example phosphoric acid, diethylphosphoric acid or phosphorous acid, or sulphur-containing acids, for example sulphuric acid, or hydrocyanic acid. Mixed anhydrides are also, for example, those with organic carboxylic acids, such as with lower alkanecarboxylic acids optionally substituted, for example by halogen, such as fluorine or chlorine, for example pivalic acid or trichloroacetic acid, or with semiesters, especially lower alkyl semiesters of carbonic acid, such as ethyl or isobutyl semiesters of carbonic acid, or with organic, especially aliphatic or aromatic, sulphonic acids, for example p-toluenesulphonic acid.

Activated esters suitable for reaction with the alcohol are, for example, esters with vinylogous alcohols (i.e. enols), such as vinylogous lower alkenols, or iminomethyl ester halides, such as dimethyliminomethyl ester chloride (manufactured from the carboxylic acid and dimethylchloromethylidene-iminium chloride of the formula $[(CH_3)_2N=CHCl]^{\oplus}Cl^{\ominus}$), or aryl esters, such as pentachlorophenyl ester, 4-nitrophenyl ester or 2,3-dinitrophenyl ester, heteroaromatic esters, such as benztriazole esters, for example 1-benztriazole ester, or diacylimino esters, such as succinylimino or phthalylimino ester.

The acylation with an acid derivative of that type, such as an anhydride, especially with an acid halide, is preferably carried out in the presence of an acid-binding agent, for example an organic base, such as an organic amine, for example a tertiary amine, such as tri-lower alkylamine, for example trimethylamine, triethylamine or ethyldiisopropylamine, or N,N-di-lower alkylaniline, for example N,N-dimethylaniline, or a cyclic tertiary amine, such as an N-lower alkylated morpholine, such as N-methylmorpholine, or a base of the pyridine type, for example pyridine, an inorganic base, for example an alkali metal or alkaline earth metal hydroxide, carbonate or bicarbonate, for example sodium, potassium or calcium hydroxide, carbonate or bicarbonate, or an oxirane, for example a lower 1,2-alkylene oxide, such as ethylene oxide or propylene oxide.

A reactive functional derivative of the alcohol to be esterified is especially a corresponding ester, preferably with a strong inorganic or organic acid and is especially a corresponding halide, for example chloride, bromide or iodide, or a corresponding lower alkyl- or aryl-sulphonyloxy compound, such as a methyl- or 4-methylphenyl-sulphonyloxy compound.

Such a reactive ester of an alcohol can be reacted with the free carboxy compound of the formula (I) or a salt, such as an alkali metal salt or ammonium salt, thereof, the reaction being carried out preferably in the presence of an acid-binding agent when using the free acid.

The above-mentioned esterification reactions are carried out in an inert, usually anhydrous solvent or solvent mixture, for example in a carboxylic acid amide, such as a formamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, if necessary while cooling or heating, for example within a temperature range of from approximately −40° C. to approximately +100° C., preferably at from approximately −10° C. to approximately +40° C., and/or in an inert gas atmosphere, for example a nitrogen atmosphere.

Furthermore, the acid derivative can, if desired, be formed in situ. Thus, for example, a mixed anhydride is obtained by treating the carboxylic acid compound having appropriately protected functional groups or a suitable salt thereof, such as an ammonium salt, for example with an organic amine, such as piperidine or 4-methylmorpholine, or a metal salt, for example an alkali metal salt, with a suitable acid derivative, such as the corresponding acid halide of an optionally substituted lower alkanecarboxylic acid, for example trichloroacetyl chloride, with a semiester of a carbonic acid semihalide, for example chloroformic acid ethyl ester or isobutyl ester, or with a halide of a di-lower alkylphosphoric acid, for example diethylphosphorobromidate, and the mixed anhydride obtainable in this manner is used without isolation.

For esterification, the hydroxy group can be converted into an acyloxy group by treating the starting material of the formula (I) with an acylating agent that introduces the desired acyl radical of an organic carboxylic acid. For this esterification, the corresponding carboxylic acid or a reactive derivative thereof, especially an anhydride, including a mixed or internal anhydride, of such an acid is used. Mixed anhydrides are, for example, those with hydrohalic acids, i.e. the corresponding acid halides, especially the chlorides, also with hydrocyanic acid, or alternatively those with suitable carbonic acid semiderivatives, such as corresponding carbonic acid semiesters (such as, for example, the mixed anhydrides formed with a halo-formic acid lower alkyl ester, such as chloroformic acid ethyl ester or isobutyl ester) or with optionally substituted lower alkanecarboxylic acids, for example those containing halogen, such as chlorine, (such as the mixed anhydrides formed with pivaloyl chloride or trichloroacetyl chloride). Internal anhydrides are, for example, those of organic carboxylic acids, i.e. ketenes, such as ketene or diketene, or those of carbamic or thiocarbamic acids, i.e. isocyanates or isothiocyanates. Further reactive derivatives of organic carboxylic acids which can be used as acylating agents are activated esters, such as suitably substituted lower alkyl esters, for example cyanomethyl ester, or suitably substituted phenyl esters, for example pentachlorophenyl or 4-nitrophenyl ester. Esterification can, if necessary, be carried out in the presence of suitable condensation agents, for example in the presence of carbodiimide compounds, such as dicyclohexylcarbodiimide, or carbonyl compounds, such as diimidazolylcarbonyl, when using free carboxylic acids and, for example, in the presence of basic agents, such as tri-lower alkylamines, for example triethylamine, or heterocyclic bases, for example pyridine, when using reactive acid derivatives. The acylation reaction can be carried out in the absence or presence of a solvent or solvent mixture, while cooling, at room temperature or while heating, and, if necessary, in a closed vessel and/or in an inert gas atmosphere, for example a nitrogen atmosphere. Suitable solvents are, for example, optionally substituted, especially optionally chlorinated, aliphatic, cycloaliphatic or aromatic hydrocarbons, such as benzene or toluene, it being possible to use suitable esterification reagents, such as acetic anhydride, also as diluents.

A hydroxy group esterified by an organic sulphonic acid, for example a lower alkanesulphonic acid, such as methanesulphonic acid, or an aromatic sulphonic acid, such as p-toluenesulphonic acid, can be formed preferably by treating the starting material of the formula (I) with a reactive sulphonic acid derivative, such as a corresponding halide, for example chloride, if necessary in the presence of an acid-neutralising basic agent, for example an inorganic or organic base, for example in a manner analogous to that used for the corresponding esters with organic carboxylic acids.

In a resulting compound of the formula (I) in which one or more functional groups are protected, the latter, for example protected carboxy and/or hydroxy groups, can be freed, optionally in stages or simultaneously, in a manner known per se, by means of solvolysis, especially hydrolysis, alcoholysis or acidolysis, or in some cases also by means of careful reduction. Silyl protecting groups are advantageously split off with fluorides, for example tetraethylammonium fluoride.

Salts of compounds of the formula (I) having salt-forming groups can be manufactured in a manner known per se. Thus, salts of compounds of the formula (I) having acid groups can be formed, for example, by treating with metal compounds, such as alkali metal salts of suitable organic carboxylic acids, for example the sodium salt of α-ethylcaproic acid, or with inorganic alkali metal or alkaline earth metal salts, for example sodium bicarbonate, or with ammonia or a suitable organic amine, preferably stoichiometric quantities or only a small excess of the salt-forming agent being used. Acid addition salts of compounds of the formula (I) are obtained in customary manner, for example by treating with an acid or a suitable anion-exchange reagent. Internal salts of compounds of the formula (I) that contain, for example, a free carboxy group can be formed, for example, by neutralising salts, such as acid addition salts, to the isoelectric point, for example with weak bases, or by treating with liquid ion-exchangers.

Salts can be converted in customary manner into the free compounds: metal and ammonium salts can be converted into the free compounds, for example, by treating with suitable acids, and acid addition salts, for example, by treating with a suitable basic agent.

The complexes of compounds of the formula (I) in which the radical —$COOR^2$ represents a free carboxy group the acid proton of which has optionally been split off are manufactured, for example, by bringing together a salt of the corresponding heavy metal, for example a halide, such as chloride, and a compound of the formula (I) in which the radical —$COOR^2$ represents a free carboxy group, or a suitable salt of that acid, for example an alkali metal salt, such as a sodium or potassium salt, advantageously in a polar solvent or solvent mixture, for example in aqueous or alcoholic, for example methanolic, solution, that has a suitable pH. The reaction temperature is normally between the melting point and the boiling point at normal pressure of the solvent or solvent mixture used, as a rule between 15° and 50° C., for example between 20° and 40° C., for example at 37°.

Since the complex compounds according to the invention are unstable both under strongly acidic conditions, for example at pH 1, and under strongly basic conditions, for example at pH 12, the pH of the reaction solution is advantageously maintained between 3 and 10, especially between 5 and 8, for example at the level of a physiological pH value, such as 7.5. The precise limits of the pH range at which the complex formation is possible depend primarily on the nature of the substances taking part in the complex formation, for example on the type of metal ion, and the solubility of the hydroxide(s) thereof. Under the mentioned optimum conditions, complex formation proceeds very rapidly so that equilibrium between the complex and the starting materials is reached within a few minutes or hours.

Mixtures of isomers can be separated into the individual isomers in a manner known per se, for example by fractional crystallisation, chromatography, etc.

Racemates can be split in a manner known per se, for example after conversion of the optical antipodes into diastereoisomers, for example by reaction with optically active acids or bases.

The invention relates also to those forms of the process in which a compound obtainable as an intermediate at any stage of the process is used as starting material and the remaining steps are carried out or the process is discontinued at any stage or a compound obtainable by the process according to the invention is produced under the reaction conditions and further processed in situ.

The starting materials are available commercially and/or known or can be manufactured by known processes.

The present invention relates also to novel starting materials and/or intermediates and processes for their manufacture. The starting materials used and the reaction conditions are preferably so chosen that the compounds mentioned in this Application as being especially preferred are obtained.

The pharmacologically acceptable compounds of the present invention can be used, for example, for the manufacture of pharmaceutical preparations which contain an effective amount of the active substance together or in admixture with inorganic or organic, solid or liquid, pharmaceutically acceptable carriers.

The pharmaceutical preparations according to the invention are those which are suitable for enteral, such as oral, administration and for parenteral, such as subcutaneous, administration to warm-blooded animals and which contain the pharmacological active substance on its own or together with a pharmaceutically acceptable carrier. The dosage of the active substance depends on the species of warm-blooded animal and on the age and individual condition, the illness to be treated and also on the mode of administration.

The novel pharmaceutical preparations contain from approximately 10% to approximately 95%, preferably from approximately 20% to approximately 90%, of the active substance. Pharmaceutical preparations according to the invention can, for example, be in unit dose form, such as dragees, tablets, capsules, suppositories or ampoules.

The pharmaceutical preparations of the present invention are manufactured in a manner known per se, for example by means of conventional mixing, granulating, dissolving or lyophilising processes. Pharmaceutical preparations for oral use can be obtained by combining the active substance with solid carriers, if desired granulating a resulting mixture and processing the mixture or granulate, if desired or necessary after the addition of suitable adjuncts, to form tablets or dragee cores. In so doing, they can also be incorporated into plastics carriers which release the active substances or allow them to diffuse in controlled amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch mucilage using, for example, maize, wheat, rice or potato starch, gelatine, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating and lubricating agents, for example silicic acid, talc, stearic acid or salts thereof, such as magnesium or calcium stearate, and/or polyethylene glycol. Dragee cores are provided with suitable coatings that are, if desired, resistant to gastric juice, there being used, inter alia, concentrated sugar solutions which optionally contain gum arabic, talc, polyvinylpyrrolidone, polyethylene glycol and/or titanium dioxide, lacquer solutions in suitable organic solvents or solvent mixtures or, for the manufacture of coatings that are resistant to gastric juice, solutions of suitable cellulose preparations, such as acetylcellulose phthalate or hydroxypropylmethylcellulose phthalate. Colouring substances or pigments can be added to the tablets or dragee coatings, for example for the purpose of identification or for indicating different doses of active substance.

The following Examples serve to illustrate the invention. Temperatures are given in degrees Centigrade.

General: m.p. determined in open capillary tubes, not corrected.

UV: Perkin-Elmer spectrometer 402; $\lambda_{max}$ data in nm (log $\epsilon$).

IR: Perkin-Elmer spectrometer 157 G; data in $cm^{-1}$.

¹HMR: Varian spectrometer HA-100 (100 MHz); chemical shifts in δ [ppm] against tetramethylsilane (TMS).
¹³C-NMR: Varian spectrometer XL-100 (25.3 MHz); chemical shifts in δ [ppm] against TMS (splitting in the off-resonance spectrum shown in brackets).
MS: intensity in % of the base peak.
TLC: silica gel-60 prepared plates $F_{254}$ manufactured by Merck; localisation of the spots generally carried out by observation in UV-light or development in iodine vapour.

EXAMPLE 1

The strain *Streptomyces antibioticus* Tü 1998 is cultured in a 10 liter fermenter (New Brunswick, model F 14) for 90 hours at 27°, 4 liters of air/min and 220 rev/min on the following nutrient solution: 2% full fat soya flour and 2% mannitol in water, pH of the nutrient solution adjusted to 7.5 with sodium hydroxide solution before sterilisation. 5% of 48 hours old pre-culture grown on the same nutrient solution is used as inoculum. For working up, 12 g of iron(III) chloride hexahydrate are added to the cultures with the pH remaining unchanged and the mixture is filtered with the addition of 1.5% Celite. The filtrate is adjusted to pH 7 with sodium hydroxide solution, saturated with sodium chloride and extracted 4 times with 2.5 liters of ethyl acetate. The extracts are concentrated in vacuo to a brown syrup which is dissolved in 50 ml of water and extracted 4 times with methylene chloride to remove the lipophilic consitituents. The aqueous phase is concentrated in vacuo to a dry powder which is dissolved in 10 ml of chloroform/methanol 1:1 and chromatographed over Sephadex LH 20. The fractions that are uniform according to TLC yield the iron complex of 2-(3'-hydroxy-pyrid-2'-yl)-4-methyl-2-thiazoline-4-carboxylate (ferrithiocin) in the form of dark brown to red powder.

For analysis, the amorphous powder is crystallised from methanol/acetonitrile/toluene to form small matted needles.
m.p. 160° (with decomposition).
TLC: $R_f$ 0.27 in chloroform/methanol/water 65:25:4.
$[\alpha]_D = 578°$ ($c = 6.4 \times 10^{-3}$ in $H_2O$).
UV (c=1%, $H_2O$) 207 (2.82), 227 shoulder (2.71), 268 shoulder (2.4), 325 (2.48), 405 (2.04), 460 shoulder (1.9).

47.5 mg of the resulting ferrithiocin are dissolved in 2 ml of $H_2O$, the solution is adjusted to pH 10 with 1 N NaOH and a saturated, aqueous solution of $KMnO_4$ is added dropwise thereto so slowly that only a faint violet colour is always present. As soon as the starting material has completely reacted (TLC), the manganese dioxide and ferric hydroxide are filtered off and the filtrate is extracted twice with 10 ml of $CHCl_3$. After concentration in vacuo, the extracts yield white crude 3-hydroxy-2-(4'-methyl-thiazol-2'-yl)-pyridine which crystallises from acetone/water to form colourless needles.
TLC: $R_f$ 0.41 in $CHCl_3$. m.p. 115°.
IR ($CHCl_3$): 1580, 1525, 1450, 1025.
¹H-NMR ($CDCl_3$): δ=2.48 (s; 3H), 6.94 (s; 1H), 7.1–7.46 (m; 2H), 8.15 (dd, $J_1$=2 Hz), $J_2$=4 Hz; 1H), 12.02 (br. s, —OH).
MS: inter alia 194 (6), 193 (14), 192.0357 (M+, calc. for $C_9H_8N_2OS$: 192.0357100), 164 (22), 72 (33), 57 (26).

EXAMPLE 2

3 ml of 1 N NaOH are added to 97 mg of ferrithiocin, the ferric hydroxide that has separated is filtered off with the aid of Celite and the filtrate is adjusted to pH 3 with conc. hydrochloric acid at 0°. In so doing, 2-(3'-hydroxy-pyrid-2'-yl)-4-methyl-2-thiazoline-4-carboxylic acid crystallises in the form of sulphur-yellow needles which are washed with ice-cold water. A sample for analysis is recrystallised from hot water/methanol.
TLC: $R_f$ 0.17 in $CHCl_3$/methanol/water 65:25:4,
m.p. 90°–92°, $\alpha_D = +30.1°$ (c=1.01, methanol)
UV ($H_2O$): 200 (4.18), 235 shoulder (3.73), 308 (3.79), 382 (3.33).
¹H-NMR (100 MHz, $d_6$-DMSO): δ=1.61 (s; 3H), 3.30 (d, J=12 Hz, 1H), 3.75 (d, J=12 Hz, 1H), 7.45 d, J=3 Hz; 2H), 8.18 (t, J=3 Hz; 1H), 12–14 (broad, 2H).
¹³C-NMR (25 MHz, $CD_3OD$): δ=25.5 (q), 40.7 (t), 87.3 (s), 126.0 (d), 128.1 (d), 135.3 (s), 141.1 (d), 156.7 (s), 172.8 (s), 180.0 (s).
MS: inter alia 240 (M+ +2.3), 238.0404 (M+ calc. for $C_{10}H_{10}N_2O_3S$: 238.041226), 193 (82), 121 (19), 92 (86), 91 (100), 65 (27), 39 (26).
$C_{10}H_{10}N_2O_3S \cdot H_2O$ (256.05). Calculated C: 46.86 H: 4.72, N: 10.93, S: 12.53. Found C: 46.58 H: 4.77, N: 10.74, S: 12.51.

2-(3'-hydroxy-pyrid-2'-yl)-4-methyl-2-thiazoline-4-carboxylic acid was manufactured as described above from 124 mg of ferrithiocin and was hydrolysed under a nitrogen atmosphere with 2 ml of 6 N hydrochloric acid for 1 hour at 90°. The residue remaining after concentration by evaporation contains, according to TLC in chloroform/methanol/water 65:25:4, 2 main products having $R_f$ 0.17 (iodine vapour and nitroprusside-Na positive, characteristic of -SH compounds [see Tonnies and J. J. Kolb, Anal. Chemistry 23, 823 (1951)] and $R_f$ 0.32 [fluorescence quenching]. The latter can be purified by prep. TLC in the same eluant system: 3-hydroxy-picolinic acid in the form of a colourless powder having a melting point of 219°–223° (with decomposition).
IR (KBr): 3430 broad, 1635, 1605, 1455.
¹H-NMR ($CD_3OD$): 7.9 (broad, 2H), 8.18 (broad, 1H).
¹³C-NMR ($CD_3OD$): 129.0 (d), 130.7 (d), 134.0 (s), 139.0 (d), 160.1 (s), 173.0 (s).
MS: inter alia 139 (M+, $C_6H_5NO_3$, 9), 121 (7), 95 (100), 93 (15), 67 (19), 44 (54).

The compound was dissolved in 2 ml of absolute dimethylformamide and, with the addition of 2 drops of $BF_3$-ether complex, was methylated with an ethereal diazomethane solution. The mixture was then diluted with 10 ml of $H_2O$ and extracted twice with ethyl acetate. The extracts were washed with $H_2O$, dried over $Na_2SO_4$ and concentrated in vacuo. The residue crystallised from ethyl acetate/hexane in the form of colourless needles having a melting point of 72°–73°. In a direct comparison (mixed m.p., TLC, IR and ¹H-NMR) the compound is found to be identical with an authentic sample of 3-hydroxy-picolinic acid methyl ester.
¹H-NMR ($CDCl_3$): 4.02 (s, 3H), 7.3–7.45 (m, 2H), 8.18–8.32 (m, 1H), 10.58 (s, 1H).
MS: inter alia: 153 (M+, $C_7H_7NO_3$, 84), 123 (73), 95 (95), 93 (100).

40 mg (0.168 mmol) of 2-(3'-hydroxy-pyrid-2'-yl)-4-methyl-2-thiazoline-4-carboxylic acid are hydrolysed as described above and the residue remaining after concentration by evaporation is chromatographed in a buffer solution of pH 5 (pyridine/glacial acetic acid 65:35 v/v per 0.1 M) over CM Sephadex C-25. The uniform fractions that can be coloured with nitroprusside-Na are concentrated in vacuo and methylated with an ethereal diazomethane solution in absolute dimethylformamide with the addition of $BF_3$-ether complex. The crude product is extracted by shaking with ethyl acetate, the extracts are washed several times with $H_2O$, are dried over $Na_2SO_4$ and concentrated by evaporation in vacuo whereupon N-formyl-2-methyl-cysteine methyl ester is obtained in the form of a colourless oil.

TLC: $R_f$ 0.41 in $CHCl_3$/ethyl acetate 1:1 (with traces of impurities).

IR ($CHCl_3$): 3390, 2850, 1735, 1690.

$^1$H-NMR ($CDCl_3$): $\delta = 1.35$ (dd, $J_1 = 8$ Hz, $J_2 = 10$ Hz; 5H), 1.67 (s; 3H), 2.96 (dd, $J_1 = 10$ Hz, $J_2 = 14$ Hz; 1H), 3.55 (dd, $J_1 = 8$ Hz, $J_2 = 14$ Hz; 1H), 3.78 (s; 3H), 6.6 (broad, 1H), 8.17 (d, $J = 2$ Hz, 1H).

Upon the addition of $D_2O$, the signals at 1.35 and 6.6 ppm disappear, the double doublets become doublets having $J = 14$ Hz and the doublet at 8.17 ppm becomes a singlet.

MS: inter alia: 178 ($[M^+ + 1]^+$, $C_6H_{12}NO_3S$, 1), 146 (3), 132 (100), 118 (21), 102 (29), 100 (62), 73 (22), 42 (54).

EXAMPLE 3

An ethereal diazomethane solution is added in the course of 20 minutes at 0° to 70 mg (0.294 mmol) of 2-(3'-hydroxy-pyrid-2'-yl)-4-methyl-2-thiazoline-4-carboxylic acid in methanol/water. Concentration by evaporation in vacuo, extraction by shaking with $CHCl_3$ from $H_2O$ and prep. TLC (silica gel, chloroform/methanol 40:1) yield 2-(3-hydroxy-pyrid-2'-yl)-4-methyl-2-thiazoline-4-carboxylic acid methyl ester in the form of a pale yellow oil.

TLC: $R_f$ 0.79 in chloroform/methanol 40:1.

UV (ethanol): 210 (4.22), 238 (3.82), 313 (4.01).

IR ($CHCl_3$): 1735, 1590, 1450, 980.

$^1$H-NMR ($CHCl_3$): $\delta = 1.68$ (s; 3H), 3.18 (d, $J = 12$ Hz; 1H), 3.77 (s; 3H), 3.80 (d, $J = 12$ Hz, 1H), 7.18–7.4 (m; 2H), 8.1–8.25 (m, 1H), 12.0 (broad s. OH).

MS: inter alia 252 ($M^+$, $C_{11}H_{12}N_2O_3S$, 24), 193 (100), 165 (4), 121 (14), 73 (23).

EXAMPLE 4

45 mg (0.189 mmol) of 2-(3'-hydroxy-pyrid-2'-yl)-4-methyl-2-thiazoline-4-carboxylic acid are treated at room temperature in methanol/water with an ethereal diazomethane solution until a yellow colour remains. Concentration by evaporation in vacuo, extraction by shaking with $CHCl_3$ from $H_2O$ and chromatography over Sephadex LH 20 with chloroform/methanol 1:1 yield 2-(3'-methoxy-pyrid-2'-yl)-4-methyl-2-thiazoline-4-carboxylic acid methyl ester in the form of a colourless oil.

TLC: $R_f$ 0.83 in chloroform/methanol/water 65:25:4.

IR ($CHCl_3$): 1730, 1600, 1580, 1465, 1430, 960.

$^1$H-NMR ($CDCl_3$): $\delta = 1.66$ (s; 3H), 3.17 (d, $J = 12$ Hz; 1H), 3.74 (d, $J = 12$ Hz; 1H), 3.77 (s; 3H), 3.88 (s; 3H), 7.32 (d; $J = 3$ Hz, 2H), 8.23 (t, $J = 3$ Hz; 1H).

MS: inter alia: 266 ($M^+$, $C_{12}H_{14}N_2O_3S$, 10), 219 (12), 207 (100), 192 (25), 166 (10), 135 (28), 73 (22).

EXAMPLE 5

The strain *Streptomyces antibioticus* Tü 1998 (DSM 1865) is cultured for 6 days at 28° C. on an agar medium of the following composition:

| | |
|---|---|
| yeast extract (Difco) | 4 g/l |
| Malt extract (Difco) | 5 g/l |
| glucose | 4 g/l |
| agar (Difco) | 20 g/l |

A 500 ml Erlenmeyer flask without baffle plates containing 100 ml of a nutrient solution consisting of 2% full fat soya flour and 2% mannitol, pH 7.5, is inoculated with the resulting slanting tube culture and incubated for 48 hours at 28° C. in a shaking machine at 250 rev/min and 50 mm displacement.

The second pre-culture stage is carried out in Erlenmeyer flasks of 2 liters capacity having 4 baffle plates. These flasks are charged with 500 ml of the above-described soya flour/mannitol nutrient solution and with 2.5% (v/v) inoculum from the first shaking flask culture. Incubation is carried out in a shaking machine at 50 mm displacement and 120 rev/min at 28° C. After 48 hours, this pre-culture has a pH of 6.7 and is used in a concentration of 5% (v/v) for inoculating a 50 liter fermenter containing 30 liters of fresh soya flour/mannitol nutrient solution.

A small fermenter of 50 liters capacity, equipped with 4 baffle plates and a six-bladed stirrer having a diameter of 115 mm is charged with 30 liters of the above-described liquid nutrient medium and sterilised at 134° C. After the addition of 1.5 liter of inoculum from the Erlenmeyer flask culture, the following fermentation conditions are maintained for 48 hours:

| | |
|---|---|
| stirring | 600 rev/min |
| overpressure | 0.5 bar |
| aeration | 1 liter of air per 1 liter of culture broth per minute |
| temperature | 28° C. |

After 48 hours, the culture solution reaches a pH of 6.4 and a cell mass of 23% (v/v) that can be centrifuged, and is used for inoculating a production fermenter.

For production batches, a fermenter of 500 liters capacity is used which is equipped with 4 baffle plates and a 6-bladed turbine stirrer of 230 mm diameter. 300 liters of the same nutrient solution as in the pre-cultures are sterilised in the fermenter and inoculated with 15 liters of the pre-culture from the small fermenter. The following fermentation conditions are maintained:

| | |
|---|---|
| stirring | 400 rev/min |
| overpressure, aeration and temperature: | analogous to those in the fermenter. |

After 77 hours, the maximum production of 2-(3'-hydroxy-pyrid-2'-yl)-4-methyl-2-thiazoline-4-carboxylic acid (salt) is achieved whereupon fermentation is discontinued. At that time, the culture solution has a pH of 6.6 and a mycelium volume (p.m.v.) that can be centrifuged of 24% (v/v). For working up, the cell material is separated off by filtration through a filter press with the addition of 2% Decalite as filtering auxiliary and is subsequently washed with a litter water. 630 liters of culture filtrate are obtained from 2 parallel batches.

600 g of iron(III) chloride hexahydrate are added to 600 liters consisting of the resulting culture filtrate and a washing solution and, after adjusting the pH to 7.0, the mixture is concentrated to a volume of 70 liters in a circular evaporator under reduced pressure. After acidifying to pH 2.5, a brownish red precipitate is separated off by filtration. The clear filtrate is poured into a column containing 70 liters of the macroreticular resin XAD-2 (manufactured by ROHM and HAAS). After adsorption at a flow rate of 70 liters/hour, washing is carried out with 140 liters of de-ionised water. The washing operation and the subsequent elution with 50% aqueous 2-propanol are carried out at a flow rate increased to 100 liters/hour. The first 60 liters of a virtually colourless eluate are discarded. 220 liters of eluate having a reddish brown colour are concentrated under reduced pressure and lyophilised, 22.5 g of residue being obtained.

The above-mentioned residue and the precipitate that was filtered off (166 g) were dissolved in 3 portions in 1 molar phosphate buffer of pH 8.8 (total 4 liters). The pH is adjusted to 8.0 by adding 2 N sodium hydroxide solution. After being saturated with sodium chloride, the mixture is extracted several times with methylene chloride until the aqueous phase no longer exhibits any red colouring. The organic phase is washed with saturated sodium chloride solution and evaporated to dryness in a rotary evaporator.

The resulting thoroughly crystallised residue (56.6 g) is dissolved in 350 ml of methanol and poured into a column (7×160 cm) packed with 1500 g of Sephadex LH-20 in methanol. Elution is carried out with methanol at a flow rate of 1 liter/hour. In the first eluate volume of 3 liters, 27.9 g of a yellow solid are separated off, and the following 0.65 liter contains 6.05 g of a colourless oil. The next 5 fractions each of 0.25 liter contain ferrithiocin which is contaminated with an oily by-product. Pure ferrithiocin is eluted in the following 10 fractions of 2.5 liters in total and, after concentration by evaporation, is obtained in pure form. Further purification of the fractions contaminated with oil yield, in addition, ferrithiocin which is uniform according to thin-layer chromatography.

For characterisation by thin-layer chromatography, MERCK silica gel plates having a layer thickness of 0.25 mm are used. Eluant systems: chloroform/methanol 4:1; chloroform/methanol/water 130:50:8. Detection of the red intrinsic colour in UV light or by staining with iodine.

30 ml of ice-cooled 1 N sodium hydroxide solution are added to 1 g of pure ferrithiocin. The ferric hydroxide which separates is separated off by filtration after the addition of filtering auxiliaries (Hyflo) and subsequently washed with a little water. The filtrate is adjusted, at 0°, to a pH of exactly 3.0 by carefully adding conc. hydrochloric acid. The precipitated yellow crystals are filtered off after 1 hour at 0°, washed with a little ice-water and dried at room temperature in a high vacuum, whereupon 2-(3'-hydroxy-pyrid-2'-yl)-4-methyl-2-thiazoline-4-carboxylic acid is obtained in the form of light yellow fine matted needles. The lyophilised mother liquors are dissolved in warm water and methanol is added, producing a further 50 mg of slightly reddish-coloured product. The crystals from the first fraction are dried over phosphorus pentoxide for 24 hours at room temperature: m.p. 115°–166°; $[\alpha]_D^{20} + 32° \pm 1°$ (c=0.715% in methanol).

EXAMPLE 6

2.283 g (13 mmol) of L-cysteine hydrochloride monohydrate (FLUKA puriss.) are dissolved in 45 ml of de-gassed distilled water whle rinsing with nitrogen and the solution is adjusted to pH 8 with approximately 10 ml of a 2 N sodium hydroxide solution. Then, a solution of 1.2 g (10 mmol) of 3-hydroxy-picolinic acid nitrile in 70 ml of methanol (MERCK p.A) is added while stirring. After a reaction period of 1½ hours at room temperature under a nitrogen atmosphere and with the exclusion of light, the reaction mixture is acidified with 10 ml of 2 N hydrochloric acid. The reaction mixture is kept in a refrigerator for 4 hours. The faintly yellow precipitate which has separated is filtered off under a nitrogen atmosphere, washed with a little ice-cooled 50% aqueous methanol and dried in a high vacuum at room temperature with the exclusion of light.

The filtrate is concentrated in vacuo and lyophilised. The resulting residue is dissolved in as concentrated a form as possible in 50% aqueous methanol. On leaving the solution to stand overnight in a refrigerator, a somewhat more intense yellow precipitate of 2-(3'-hydroxy-pyrid-2'-yl)-2-thiazoline-4-carboxylic acid forms which is filtered off and dried in the manner described above.

The 3-hydroxy-picolinic acid nitrile used is manufactured from furfural in the manner prescribed by Niels Clauson-Kaas and collaborators (Acta Chemica Scandinavica 19, 1965, 1147–1152).

EXAMPLE 7

The isomeric 2-(3'-hydroxy-pyrid-2'-yl)-2-thiazoline-4-carboxylic acid is obtained by reacting 0.526 g (4.4 mmol) of 3-hydroxy-picolinic acid nitrile with 1.0 g (5.7 mmol) of D-cysteine hydrochloride monohydrate (FLUKA puriss.) in a manner analogous to that described in Example 6.

EXAMPLE 8

In a manner analogous to that described in Example 6, 2.05 g (13 mmol) of D,L-cysteine hydrochloride (purum, FLUKA) are reacted with 1.2 g (10 mmol) of 3-hydroxypicolinic acid nitrile, the optically inactive 2-(3'-hydroxy-pyrid-2'-yl)-2-thiazoline-4-carboxylic acid being obtained in good yield.

EXAMPLE 9

2-(3'-methoxy-pyrid-2'-yl)-2-thiazoline-4-carboxylic acid is obtained by reacting 3-methoxy-picolinic acid nitrile with 1.3 molar equivalents of D,L-cysteine hydrochloride according to Example 8. 3-methoxy-picolinic acid nitrile is manufactured by adding an ethereal diazomethane solution in excess to a methanolic solution of 3-hydroxy-picolinic acid nitrile at room temperature. After leaving the reaction mixture to stand overnight it is evaporated to dryness in vacuo and used for the above-mentioned reaction without further purification.

EXAMPLE 10

Analogously to Example 6, 1 g (5.83 mmol) of α-methyl-D,L-cysteine hydrochloride is reacted with 0.585 g (4.86 mmol) of 3-hydroxy-picolinic acid nitrile. The reaction solution, acidified with 2 N hydrochloric acid, is freed of methanol after 1 hour at room temperature under reduced pressure and poured into a column containing 200 ml of XAD-2 resin manufactured by ROHM and HAAS. Elution is carried out in succession with distilled water, 10% aqueous isopropanol and 50% aqueous isopropanol. By concentrating the eluate under reduced pressure and lyophilising the aqueous residue, 2-(3'-hydroxy-pyrid-2'-yl)-4-methyl-2-thiazoline-4-carboxylic acid is obtained The manufacture of α-methyl-cysteine is described in the Ph.D. dissertation of John F. G. Diederich, University of Windsor, Canada (1966). See also R. Thiberk, J. F. G. Diederich and K. G. Rutherford, Can. J. Chem. 43, 206 (1965).

In an analogous manner, (D)- and (L)-2-(3'-hydroxy-pyrid-2'-yl)-4-methyl-2-thiazoline-4-carboxylic acid are obtained respectively starting from the appropriate one of the optical antipodes of α-methyl-D,L-cysteine, which can be obtained in a manner known per se by splitting the racemate.

EXAMPLE 11

0.24 g (1 mmol) of 2-(3'-hydroxy-pyrid-2'-yl)-2-thiazoline-4-carboxylic acid is heated at 50° C. for 14 hours with 0.485 g (1.5 mmol) of N,N'-dicyclohexyl-O-(2-trimethylsilylethyl)-isourea and 5 ml of absolute dioxan. After cooling in a refrigerator, the precipitated N,N'-dicyclohexylurea is filtered off. The filtrate is evaporated to dryness and the residue is purified by chromatography over silica gel using chloroform with an increasing content of methanol. The fractions that are uniform according to thin-layer chromatography are combined and evaporated to dryness, yielding 2-(3'-methoxy-pyrid-2'-yl)-2-thiazoline-4-carboxylic acid β-(trimethylsilyl)-ethyl ester.

The N,N'-dicyclohexyl-O-(2-trimethylsilylethyl)-isourea used as reagent is obtained in the following manner:

A mixture of 780 mg (3.79 mmol) of N,N'-dicyclohexylcarbodiimide, 0.6 ml (4.17 mmol; 1.1 equivalent) of 2-trimethylsilylethanol and 60 mg of copper(I) chloride is stirred at room temperature for 105 minutes, diluted with 3 ml of petroleum ether and filtered over a column of neutral aluminium oxide (with subsequent washing with petroleum ether). After evaporating off the solvent, the mentioned isourea derivative remains in the form of a faintly greenish oil. A small sample of this material distils in a flanged flask at approximately 125°/0.09 torr (bath temperature).

EXAMPLE 12

0.41 g (1.2 mmol) of the crude amorphous β-trimethylsilylethyl ester that is obtained according to the method described in Example 11, is dissolved in 5 ml of absolute tetrahydrofuran under a nitrogen atmosphere and cooled to −78° C. While stirring thoroughly, 2.9 ml of a solution of lithium N-isopropylcyclohexylamide (1.3 mmol), freshly prepared from n-butyllithium and N-isopropyl-cyclohexylamine, in absolute tetrahydrofuran are slowly added. After a reaction period of 10 minutes at −78° C., 2 ml of a 30% solution (w/v) of methyl iodide in absolute tetrahydrofuran are added and the reaction solution is allowed to warm up slowly to −25° C. Then, dilution is carried out with 50 ml of methylene chloride and 30 ml of cold 1 M phosphate buffer of pH 5.0. Having been separated off, the organic phase is washed with fresh phosphate buffer and with aqueous sodium chloride solution, dried over sodium sulphate and evaporated to dryness under reduced pressure. After purifying the amorphous crude product by chromatography over a column of 100 g of silica gel that has been acid-washed, methylene chloride and increasing additions of isopropanol being used for elution, 2-(3'-methoxy-pyrid-2'-yl)-4-methyl-2-thiazoline-4-carboxylic acid β-(trimethylsilyl)-ethyl ester is obtained.

EXAMPLE 13

0.53 g (1.5 mmol) of the amorphous 2-(3'-methoxy-pyrid-2'-yl)-4-methyl-2-thiazoline-4-carboxylic acid β-(trimethylsilyl)-ethyl ester obtained according to Example 12, which is uniform according to thin-layer chromatography, are dissolved with 6 ml of a 0.5 N solution of tetraethylammonium fluoride in absolute dimethylformamide and heated at 30° C. for one hour. The reaction mixture is then diluted with 30 ml of a 2 M phosphate buffer of pH 4.0 and poured into a column packed with 400 ml of XAD-2 resin. The column is eluted in succession with distilled water, 10% aqueous isopropanol and, finally, with 50% aqueous isopropanol. The course of an elution is monitored by measuring the conductivity and the UV-absorption at 254 nm in through-flow cells. The fractions that contain the desired product are concentrated under reduced pressure and lyophilised. The residues are analysed by thin-layer chromatography over silica gel plates (solvents: chloroform/methanol/water 65:25:4). The uniform fractions are taken up in absolute dioxan and combined. After lyophilisation thereof, 2-(3'-methoxy-pyrid-2'-yl)-4-methyl-2-thiazoline-4-carboxylic acid is obtained.

EXAMPLE 14

Manufacture of 1000 capsules each containing 260 mg of the active ingredients:

| Composition | |
|---|---|
| 2-(3'-hydroxy-pyrid-2'-yl)-4-methyl-2-thiazoline-4-carboxylic acid | 260 g |
| talc | 36 g |
| wheat starch | 24 g |
| magnesium stearate | 16 g |
| lactose | 4 g |
| | 340 g |

PREPARATION

The pulverulent substances are forced through a sieve having a mesh width of 0.6 mm and mixed thoroughly. Gelatine capsules are each filled with 340 g of this mixture using a capsule filling machine.

EXAMPLE 15

Manufacture of 1000 capsules each containing 105 mg of the active substances:

| Composition | |
|---|---|
| 2-(3'-hydroxy-pyrid-2'-yl)-4-methyl-2-thiazoline-4-carboxylic acid | 105 g |
| ethylcellulose | 3 g |
| stearic acid | 3 g |
| | 111 g |

Preparation

The ethylcellulose and the stearic acid are dissolved in 120 ml of methylene chloride, the antibiotic is added, and the mass is forced through a sieve having a mesh width of 0.6 mm at approximately 40°, during which the methylene chloride evaporates. 156 mg of the resulting granulate are placed in 0.5 ml gelatine capsules with the aid of a capsule filling machine.

We claim:
1. A 2-(3'hydroxy-pyrid-2'-yl)-2-thiazoline-4-carboxylic acid derivative of the formula

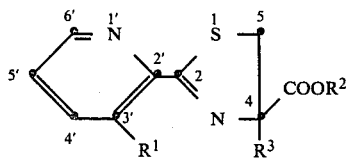

(I)

in a racemic or optically active form, in which R₁ represents free hydroxy, hydrocarbyloxy, hydrocarbylcarbonyloxy or hydrocarbyloxycarbonyloxy, hydrocarbyl denoting an aliphatic radical having 1–7 carbon atoms, a cycloaliphatic radical having 3 to 8 ring members, a phenyl radical, or an aliphatic radical having 1–7 carbon atoms that is substituted by at least one cycloaliphatic radical having 3 to 8 ring members or by at least one phenyl radical, or in which $R^1$ represents monocyclic aromatic or lower aliphatic sulphonyloxy; $R^2$ represents hydrogen, an aliphatic radical having 1–7 carbon atoms, a cycloaliphatic radical having 3 to 8 ring members, a phenyl radical or an aliphatic radical having 1–7 carbon atoms that is substituted by at least one cycloaliphatic radical having 3 to 8 ring members or by at least one phenyl radical; and $R^3$ represents hydrogen or lower alkyl; or a salt of such a derivative or a heavy metal ion complex of said derivative having a free 4-carboxy group.

2. A compound of the formula (I) according to claim 1 in which $R^1$ represents free hydroxy, alkoxy having 1–12 carbon atoms, monocyclic aromatic sulphonyloxy, lower alkylsulphonyloxy, hydrocarbylcarbonyloxy or hydrocarbyloxycarbonyloxy, hydrocarbyl representing lower alkyl, cycloalkyl having 3–8 carbon atoms, a monocyclic aromatic hydrocarbon radical or phenyl-lower alkyl, and in which $R^2$ represents lower alkyl, cycloalkyl of 3–8 carbon atoms, a monocyclic aromatic hydrocarbon radical, phenyl-lower alkyl or hydrogen, and $R^3$ represents hydrogen or lower alkyl, or a salt of such a compound or a heavy metal ion complex of such a compound having a free 4-carboxy group.

3. A compound of the formula (I) according to claim 1 in which $R^1$ represents free hydroxy, lower alkoxy or lower alkanoyloxy, or phenyloxy or benzyloxy each of which is unsubstituted or substituted by halogen, lower alkyl or lower alkoxy, and in which $R^2$ represents hydrogen, lower alkyl, or a phenyl or phenyl-lower alkyl radical, or a salt of this compound or a heavy metal ion complex of such a compound having a free 4-carboxy group.

4. A compound of the formula (I) according to claim 1 in which $R^1$ represents free hydroxy or lower alkoxy, $R^2$ represents hydrogen or lower alkyl and $R^3$ represents methyl, or a salt of this compound or an iron ion complex of said compound having a free 4-carboxy group.

5. A compound of the formula (I) according to claim 1 in which $R^1$ represents hydroxy or methoxy, $R^2$ represents hydrogen or methyl and $R^3$ represents hydrogen or methyl, or a salt thereof.

6. A compound of the formula (I) according to any one of claims 1 to 5 in which $R^2$ represents hydrogen, or a salt thereof.

7. A compound of the formula (I) according to claim 1, 2 or 5 in which $R^3$ represents methyl, or a salt thereof.

8. A compound of the formula I according to claim 1, 2 or 5 in which $R^3$ represents hydrogen, or a salt thereof.

9. A compound according to claim 1, namely the optically active form having the same sign of optical rotation as that obtainable by the fermentation of the strain Streptomyces antibioticus Waksman et Henrici Tü 1998 deposited under the designation dsm 1865 at the Deutsche Sammlung von Mikroorganismen, on June 16, 1980.

10. A compound according to claim 2, namely a salt and the iron (III) complex (ferrithiocin) of 2-(3'-hydroxy-pyrid-2'-yl)-4-methyl-2-thiazoline-4-carboxylic acid.

11. A compound of the formula (I) according to claim 6 in which $R^3$ represents methyl, and a salt thereof.

12. A compound of the formula (I) according to claim 6 in which $R^3$ represents hydrogen, and a salt thereof.

13. A pharmaceutically acceptable salt of a compound of the formula (I) according to claim 1 or 5.

14. The sodium salt of 2-(3'-hydroxy-pyrid-2'-yl)-4-methyl-2-thiazoline-4-carboxylic acid according to claim 1.

15. A compound according to claim 1, 2, 3, 4 or 5, wherein $R^1$ represents free hydroxy, or a pharmaceutically acceptable salt thereof.

16. A compound according to claim 1, namely 2-(3'-hydroxy-pyrid-2'-yl)-4-methyl-2-thiazoline-4-carboxylic acid.

17. A compound according to claim 2, namely 2-(3'-hydroxy-pyrid-2'-yl)-4-methyl-2-thiazoline-4-carboxylic acid methyl ester.

18. A compound according to claim 2, namely 2-(3'-methoxy-pyrid-2'-yl)-4-methyl-2-thiazoline-4-carboxylic acid methyl ester.

19. A compound according to claim 2, namely 2-(3'-hydroxy-pyrid-2'-yl)-2-thiazoline-4-carboxylic acid.

20. Use of a compound of the formula (I) according to claim 1, 10, or 15 or a pharmaceutically acceptable salt thereof for the abstraction of heavy metals from the organism of warm-blooded animals including that of man by oral or parenteral administration of an effective dose.

21. A pharmaceutical preparation for oral or parenteral administration for the abstraction of heavy metals from the organism of warm-blooded animals including that of man, which pharmaceutical preparation contains an effective dose of a compound of the formula (I) according to claim 1, 16 or 19, or a pharmaceutically acceptable carrier.

22. A pharmaceutical preparation according to claim 21 for the abstraction of iron from the human organism.

* * * * *